(12) United States Patent
Säll et al.

(10) Patent No.: US 10,792,441 B2
(45) Date of Patent: Oct. 6, 2020

(54) RECORDING UNIT

(71) Applicant: Carebay Europe Ltd, Sliema (MT)

(72) Inventors: Daniel Säll, Segeltorp (SE); Daniel Carlsson, Enskede (SE); Ola Hallström, Värmdö (SE)

(73) Assignee: SHL MEDICAL AG, Zug (CH)

( * ) Notice: Subject to any disclaimer, the term of this patent is extended or adjusted under 35 U.S.C. 154(b) by 226 days.

(21) Appl. No.: 15/959,720

(22) Filed: Apr. 23, 2018

(65) Prior Publication Data

US 2018/0236185 A1    Aug. 23, 2018

(30) Foreign Application Priority Data

Feb. 22, 2017   (EP) ..................... 17157417

(51) Int. Cl.
    *A61M 5/50*      (2006.01)
    *A61M 5/20*      (2006.01)
    (Continued)

(52) U.S. Cl.
    CPC ............ *A61M 5/5086* (2013.01); *A61M 5/20* (2013.01); *A61M 5/2033* (2013.01); *A61M 2005/3126* (2013.01); *A61M 2205/332* (2013.01); *A61M 2205/3306* (2013.01); *A61M 2205/3553* (2013.01); *A61M 2205/3561* (2013.01); *A61M 2205/3584* (2013.01); *A61M 2205/3592* (2013.01); *A61M 2205/50* (2013.01); *A61M 2205/52* (2013.01); *A61M 2205/581* (2013.01);
    (Continued)

(58) Field of Classification Search
    CPC .... A61M 5/5086; A61M 5/20; A61M 5/2033; A61M 2205/3306; A61M 2205/52; A61M 2005/3126; A61M 2205/50; A61M 2205/332; A61M 2205/581; A61M 2205/3592; A61M 2205/3584; A61M 2205/3561; A61M 2205/3553; A61M 2205/582; H04W 84/042; H04W 84/12; H04W 4/80
See application file for complete search history.

(56) References Cited

U.S. PATENT DOCUMENTS

| | | | |
|---|---|---|---|
| 2014/0194826 A1* | 7/2014 | Nielsen | A61M 5/31553 604/189 |
| 2019/0217022 A1* | 7/2019 | Gentz | A61M 5/3243 |
| 2019/0255252 A1* | 8/2019 | Gentz | A61M 5/315 |

FOREIGN PATENT DOCUMENTS

WO     2018085952 A1 †   5/2018

\* cited by examiner
† cited by third party

*Primary Examiner* — Amber R Stiles
(74) *Attorney, Agent, or Firm* — McDonnell Boehnen Hulbert & Berghoff LLP

(57) ABSTRACT

The present invention relates to a recording unit arranged to be connected to a medicament delivery device, which recording unit comprises a generally elongated housing (10; 90) having dimensions so as to enclose at least a distal part of the medicament delivery device (50), the recording unit comprising a recording mechanism (60; 120) provided with an electronic circuit (64; 134) and arranged at a distal end inside said housing, said electronic circuit comprising an activation element (40; 108) operably arranged to activate said electronic circuit (64; 134) when said medicament delivery device is inserted in said housing, said electronic circuit (64; 134) comprising sensor elements (80; 140) capable of sensing status changes of said medicament delivery device during use.

20 Claims, 9 Drawing Sheets

(51) Int. Cl.
  *H04W 4/80* (2018.01)
  *H04W 84/12* (2009.01)
  *H04W 84/04* (2009.01)
  *A61M 5/31* (2006.01)
(52) U.S. Cl.
  CPC ......... *A61M 2205/582* (2013.01); *H04W 4/80* (2018.02); *H04W 84/042* (2013.01); *H04W 84/12* (2013.01)

RECORDING UNIT

CROSS REFERENCE TO RELATED APPLICATION

This application claims priority to European Application No. 17157417.1, filed Feb. 22, 2017, which is herein incorporated by reference in its entirety.

TECHNICAL AREA

The following description relates to a recording unit designed to be releasably connected to a medicament delivery device in a simple and intuitive fashion.

BACKGROUND OF INVENTION

Many of the modern medicament delivery devices on the market today have been developed with the end user, i.e. the patient or a helper of a patient, in mind. Thus many of the modern medicament delivery devices have a number of features that facilitates the use and handling of the medicament delivery devices.

A further aspect on modern medicament delivery devices is the desire to obtain information regarding the use and the status such that on the one hand the patients behaviour and adherence to a treatment scheme can be monitored, recorded and made available to a care taker or health service and on the other hand to aid the patient in the handling of the medicament delivery device and aiding regarding the adherence.

These features may well be realised by electronic circuits and sensors incorporated inside a housing of a medicament delivery device. This approach is mostly feasible from an economic perspective if the medicament delivery device is a reusable device that can be reloaded with medicament containers. For disposable medicament delivery devices, the cost will probably be too high to incorporate electronics in such devices.

Another approach is to provide functionality and "intelligence" to a medicament delivery device by adding or connecting a separate monitoring or recording unit to an existing medicament delivery device. This has several advantages. One is that the unit may be used with a large number of medicament delivery devices which is positive when disposables are used. After a dose delivery by a disposable medicament delivery device, the recording unit may be detached and the disposable medicament delivery device is discarded. For the subsequent dose delivery, a new disposable medicament delivery device is provided and the recording unit is attached.

Another advantage is that the medicament delivery devices do not have to be modified in order to function with a recording unit. This would otherwise be a problem since medicament delivery devices approved by the authorities may not be altered or modified in any way. Also, a new medicament delivery device containing a recording unit must be approved by the authorities before it may enter the market.

In order to provide medicament delivery devices already on the market with recording or monitoring functions, a number of add-on solutions have been devised. Especially regarding insulin pens, a number of attachable solutions have been developed and are on the market. Most of these solutions may detect when a dose is administered by detecting the movement of a dose setting and dose delivering button that often is positioned at a distal end of the medicament delivery device. They are then placed in the vicinity of the dose setting button in order to detect the movement. The detected use of the medicament delivery device then often leads to a time stamp being created and a timer function being activated. This information may then be used in connection with pre-set time intervals between dose delivery occurrences such that the recording unit may alarm a user if the subsequent dose delivery occurrence has been passed. Many of these recording units further comprise data communication features so that they may communicate and handle data between the unit and a smart device for instance.

One such monitoring unit that may be releasably connected to a medicament delivery device is disclosed in document U.S. Pat. No. 9,101,723. Here an electronics module is attached to an outer surface of a medicament delivery device. The electronics module is arranged with some sort of pressure sensor, alternatively vibration sensor. The electronics module is designed such that the sensor is placed so that it can detect mechanical "click sounds" from engaging parts of the medicament delivery device when e.g. a dose is set and/or delivered.

There are some drawbacks with the design of U.S. Pat. No. 9,101,723. The monitoring unit only detects and registers the set dose. Any other activities are not registered or detected, such as start of injection, end of injection, withdrawal of the injector from the dose delivery site etc. Such information may in many instances be very important to both a user and/or health care provider. There is thus room for improvements in this technical field.

BRIEF DESCRIPTION OF INVENTION

The aim of the present invention is to remedy the drawbacks of the state of the art medicament delivery devices. This aim is obtained by a recording unit having the features of the independent claim. Preferable embodiments of the invention form the subject of the dependent patent claims.

According to one aspect, it comprises a recording unit arranged to be connected to a medicament delivery device. The recording unit may preferably comprise a generally elongated housing having dimensions so as to enclose at least a distal part of the medicament delivery device. Moreover, the recording unit may comprise an electronic circuit arranged at a distal end inside the housing, where the electronic circuit may comprise an activation element operably arranged to activate the electronic circuit when the medicament delivery device is inserted in housing. The electronic circuit may comprise sensor elements capable of sensing status changes of the medicament delivery device during use.

With this solution, a recording unit that is easy to adapt to many different medicament delivery devices is obtained. The outer housing may be developed in many ways and dimensions to fit different medicament delivery devices. A further advantage is that the recording unit is activated when the medicament delivery device is placed inside the outer housing, which should be just before use of the medicament delivery device. This means that a power source of the recording unit will not run the risk of being depleted before the recording unit is used, due to e.g. unintentional premature activation.

The recording unit may further comprise a resilient force member arranged between the medicament delivery device and the electronic circuit for urging the medicament delivery device in the proximal direction. Moreover, the recording unit may further comprise a locking element for locking the medicament delivery device in the proximal direction when inserted into the housing. In addition the recording unit may comprise a holding element for releasably holding the locking element in a locking position. This solution provides for a reliable and easy to use function that will connect the medicament delivery device to the recording unit in a reliable and yet easily detachable way, which is in particular an advantage with the use of disposable medicament delivery devices. Preferably, the holding element may be arranged slidable inside the housing between a holding position where the locking element is in a locking position and a release position wherein the locking element may be moved out of engagement with the medicament delivery device.

According to one aspect of the invention, the sensor element may comprise a force sensor capable of sensing force variations in the medicament delivery device during use. Force variations may be due to a number of handling aspects such as removal of a safety cap, pressing the medicament delivery device against a dose delivery site, activating a force unit for performing an injection, and withdrawal of the medicament delivery device from the dose delivery site. Thus, a lot of information may be obtained from the sensor regarding different handling positions.

As an alternative, the sensor element may comprise a movement sensor capable of sensing movement of the medicament delivery device relative the recording unit during use. The medicament delivery device is moving somewhat in relation to the recording unit during use, which may be utilized for detecting the status of the medicament delivery device. Further, also individual components of the medicament delivery device may move relative each other during the use of the medicament delivery device, which may also be utilized for detecting the status of the medicament delivery device.

According to a further aspect, the recording unit may comprise a user communication element capable of providing a user with information regarding the status of the medicament delivery device. This information may be connected for instance to a dose delivery sequence such that detection of the start of e.g. an injection will start an audible signal that may last a predetermined time period based on predicted injection time. As an alternative, if a sensor is capable of detecting the end of the injection movement, the audible signal may end at that moment. As a further alternative, the signal may continue for a predetermined time period, urging the user to keep the medicament delivery device at the injection site, which ascertains that the whole dose quantity is delivered into the tissue before removing the medicament delivery device. As an alternative or in combination, the user communication element may provide tactile information such as vibrations.

According to a further aspect, the recording unit may comprise a communication module capable of communicating with external communication devices. In this regard, the communication module may comprise near range communication technologies that for example could communicate with smart devices in the vicinity. These smart devices may in that regard be arranged with applications and programs that are capable of handling and processing information obtained from the sensors of the recording unit. As an alternative, the communication module may comprise cellular radio communication technologies and/or wireless local area network communication technologies. If so, the recording unit may be capable of communicating via the internet to external data management centres, such that for instance the caretakers of the user may obtain information from the recording unit of the user.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

DETAILED DESCRIPTION OF THE INVENTION

Figure 1:
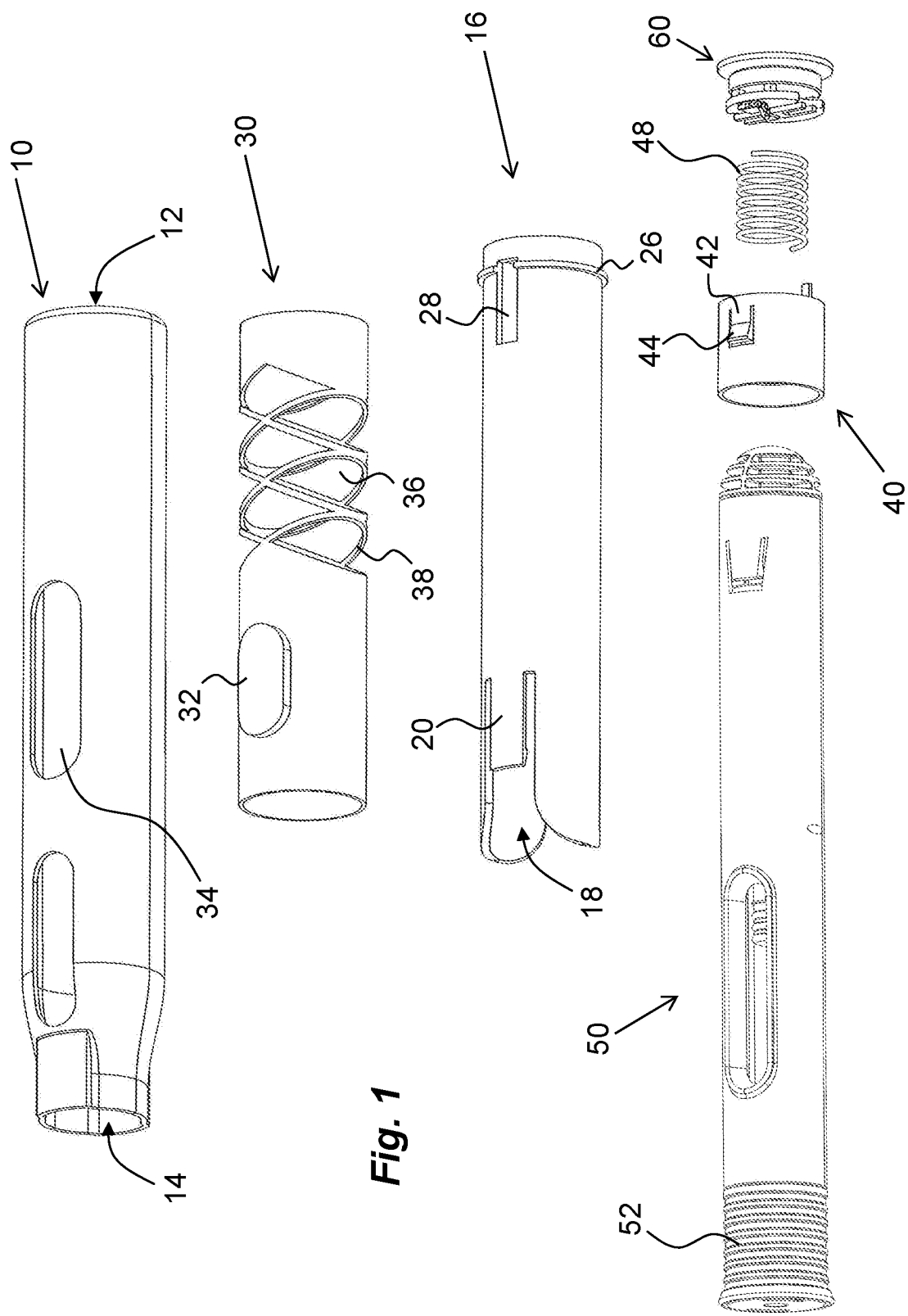
FIG. 1 is an exploded view of a first embodiment of a recording unit.
Figure 2:
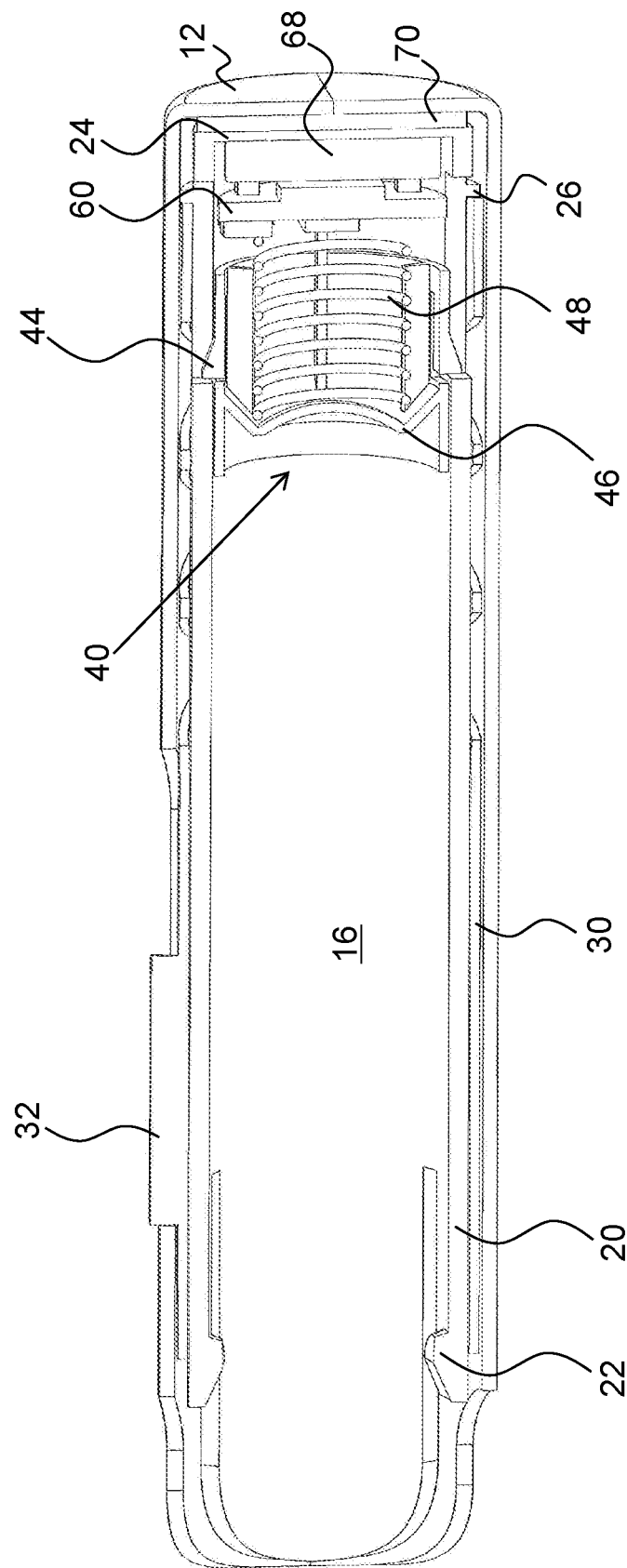
FIG. 2 is a cross-sectional view of the recoding unit of FIG. 1.
Figure 3:
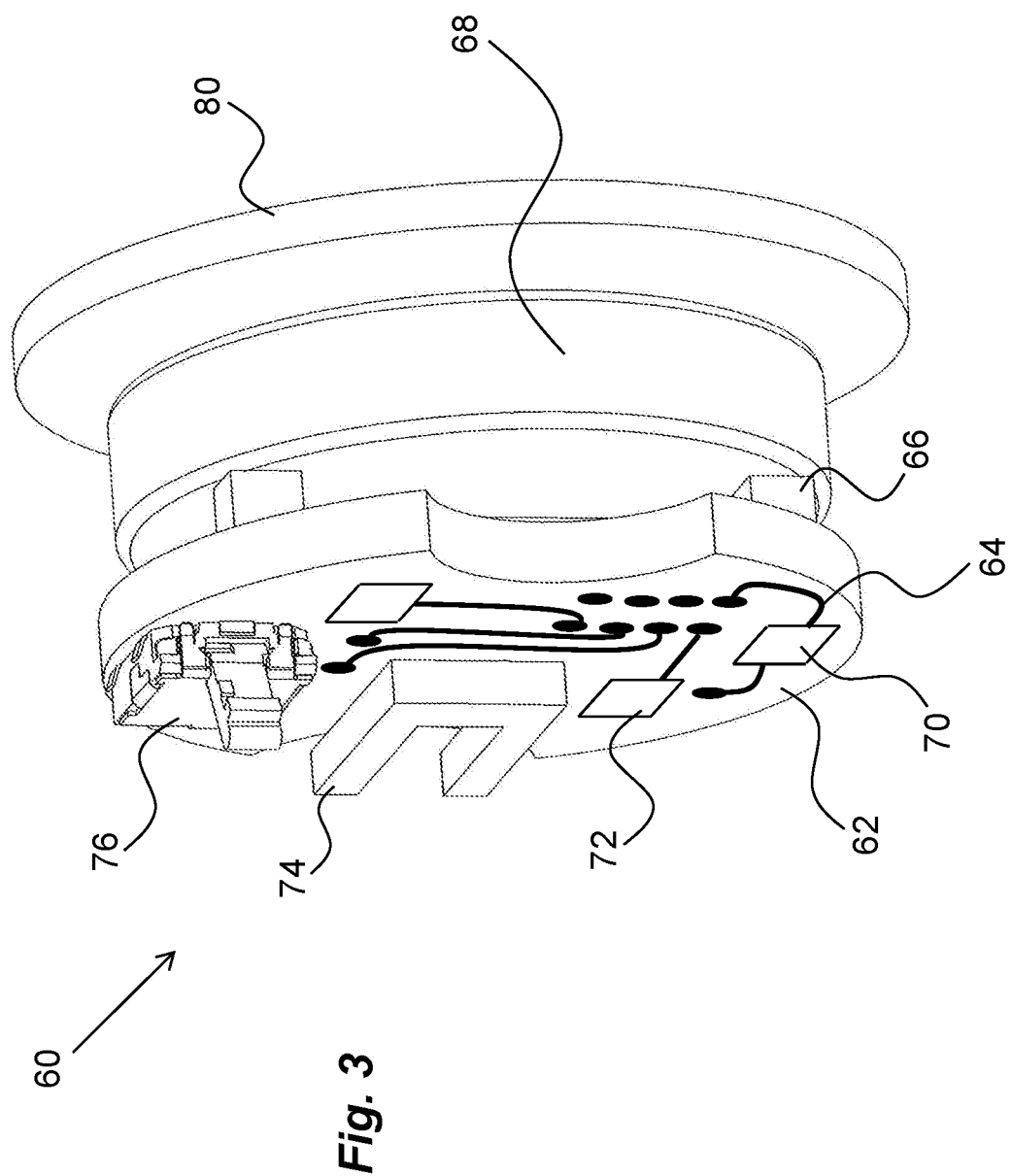
FIG. 3 is a perspective view of a recording mechanism comprised in the recording unit of FIG. 1.
Figure 4:
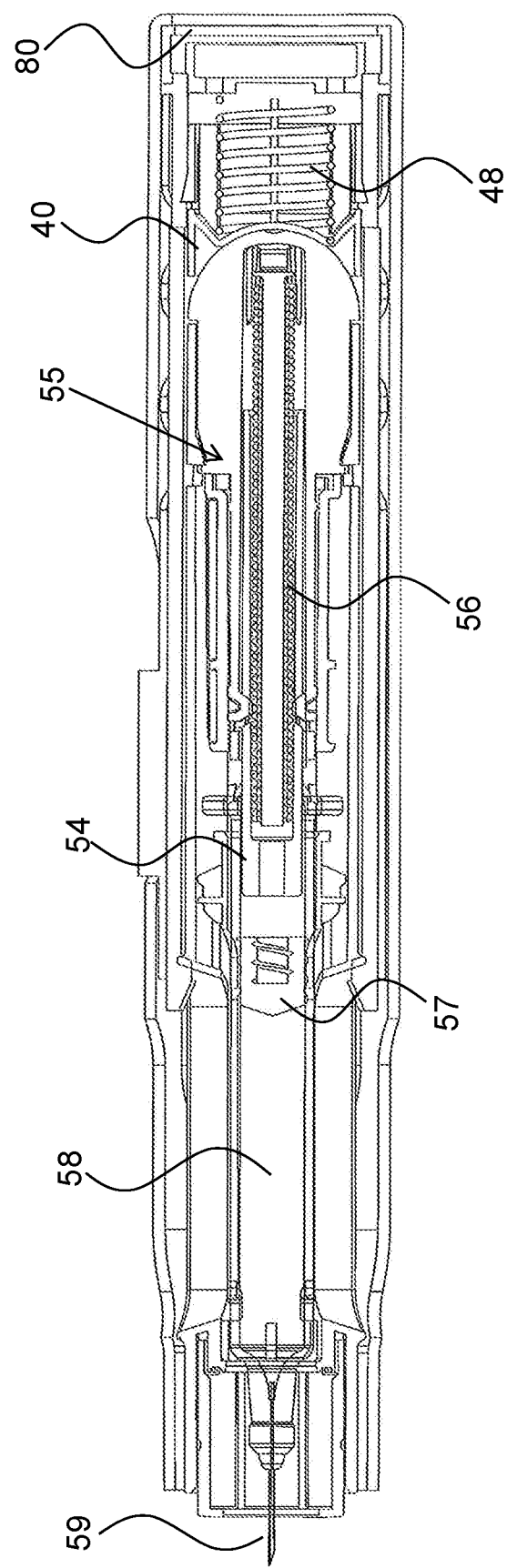
FIG. 4 is a cross-sectional view of the recording unit of FIG. 1, with a medicament delivery device inserted.
Figure 5:
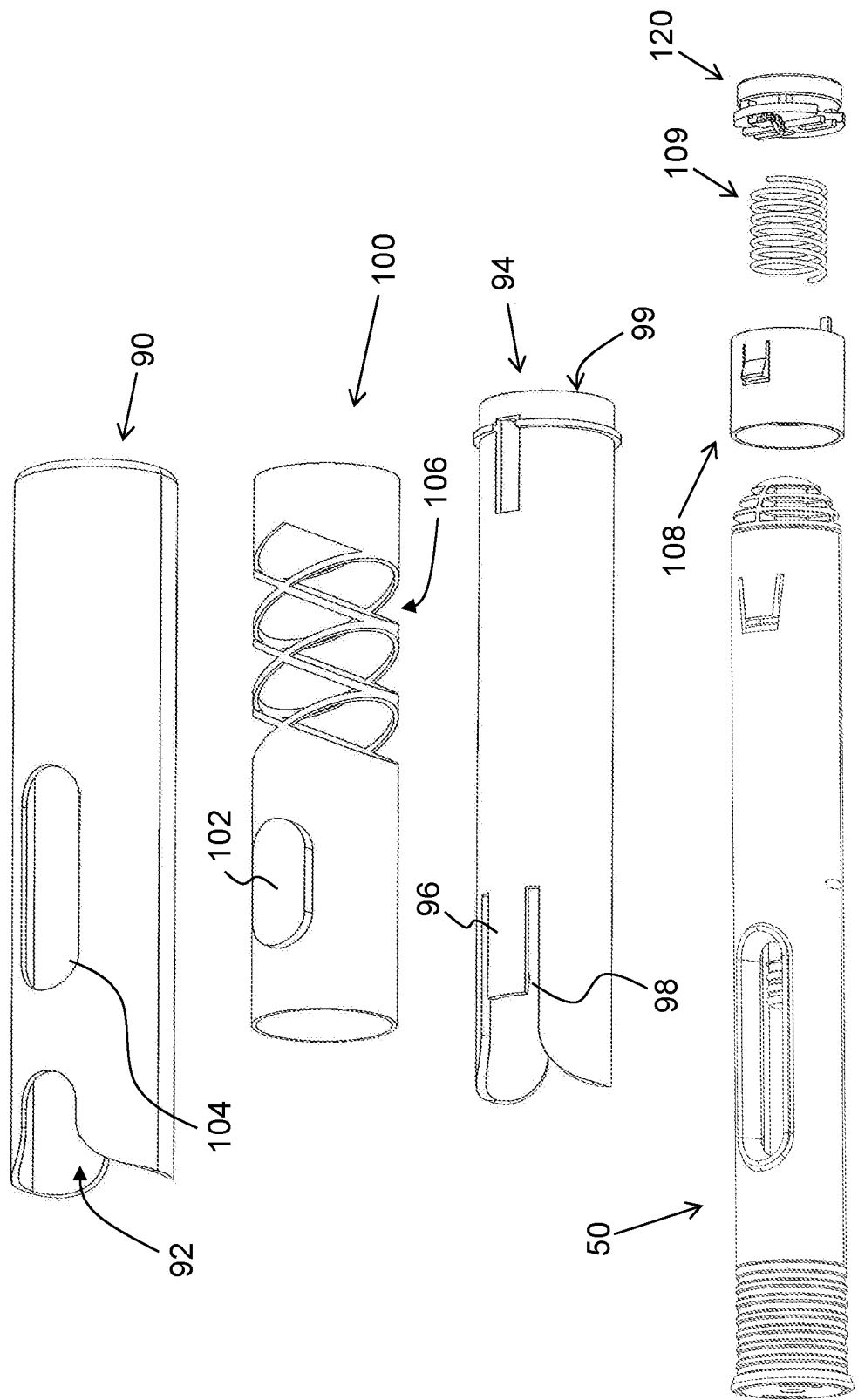
FIG. 5 is an exploded view of a second embodiment of a recording unit.
Figure 6:
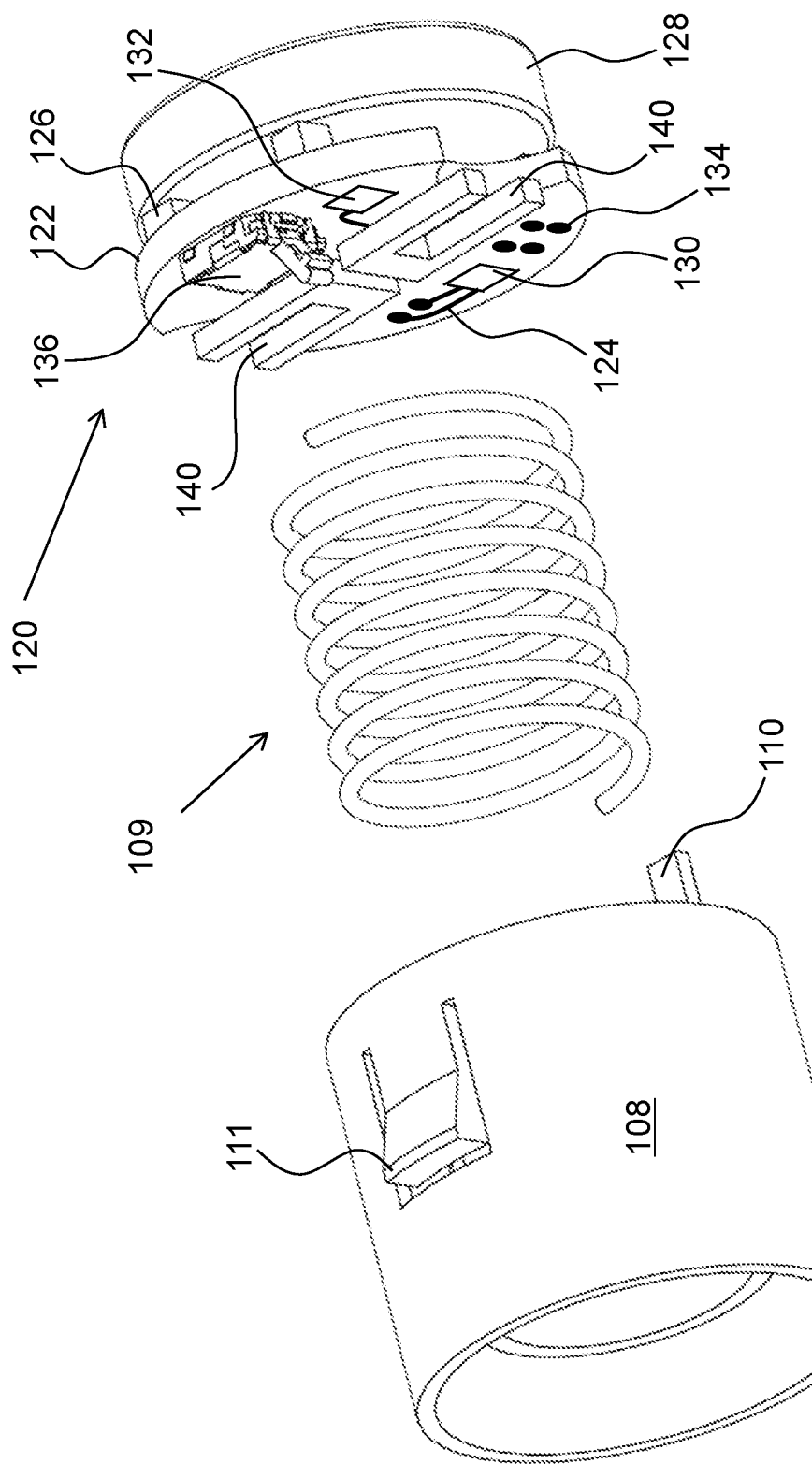
FIG. 6 is a perspective view of a recording mechanism comprised in the recording unit of FIG. 5, FIGS. 7-9 are functional views of a distal area of the recording unit of FIG. 5 with a medicament delivery device.

A first embodiment of a recording unit shown in the drawings 1 to 4 comprises an outer generally tubular outer housing 10. The outer housing 10 is arranged with a distal end wall 12 and a proximal passage 14. A generally tubular locking element 16 is arranged to fit into the outer housing. It comprises a proximal passage 18 provided with proximally extending arms 20 arranged with radially inwardly protruding ledges 22, the function of which will be described below. The distal end of the locking element 16 is provided with an end wall 24 and a circumferential outwardly extending ledge 26 on its outer surface at a distal area thereof. Moreover generally rectangular cut-outs 28 are arranged adjacent the circumferential ledge 26.

Further, a generally tubular release element 30 is arranged to fit into and coaxial with the outer housing 10 and having the locking element 16 coaxial with an inside the release element 30. On its outer surface, the release element 30 is provided with an outwardly extending protrusion 32 arranged to fit into an elongated passage 34 on a side surface of the outer housing 10, such that the protrusion 32 may slide in the longitudinal direction when manually operated as will be described. An area of the release element 30 is provided with areas 36 with removed material forming a band-shaped structure 38 which provides a resiliency between a proximal part and a distal part of the release element 30. The distal end of the release element 30 is arranged to abut a proximally directed surface of the circumferential ledge 26 of the locking element 16. Further a generally tubular support element 40 is arranged inside the locking element 16 at a distal area thereof. The support element 40 is provided with proximally extending tongues 42, which tongues 42 are arranged with outwardly directed wedge-shaped protrusions 44. The wedge-shaped protrusions 44 are arranged to fit into the rectangular cut-outs 28 in the locking element 16, where proximally directed surfaces of the wedge-shaped protrusions 44 form stop surfaces for the support element 40 as will be described below.

The support element 40 is further arranged with a transversal wall 46 preferably having a shape that corresponds to the shape of a distal end of a medicament delivery device 50 to be used with the present invention. The support element 40 is urged in the proximal direction by a force element that in the embodiment shown is a compression spring 48. The locking element 16 is also urged in the proximal direction by the wedge-shaped protrusions 44 of the support element 40 acting on the edges of the rectangular cut-outs 28. However, the locking element 16 is prevented from moving in the proximal direction in relation to the outer housing 10 since the distal end of the release element 30 is in contact with a proximal surface of the circumferential ledge 26 of the locking element 16 and that the protrusion 32 on the release element 30 is positioned at the most proximal location in the elongated passage 34 of the outer housing 10.

The distal end of the compression spring 48 is in contact with a recording mechanism 60. The recording mechanism 60 comprises a printed circuit board 62 provided with an electronic circuit 64. On the distal side of the printed circuit board 62, support elements 66 are arranged providing a space between the distal surface of the printed circuit board 62 and a power source 68 in the form of a button cell. The distal surface of the button cell 68 is in contact with a proximally directed surface of the end wall 24 of the locking element 16. The electronic circuit 64 is provided with a micro-controller unit 70 or MCU arranged to perform different functions based on program code. The electronic circuit 64 is further arranged with memory storage elements 72 in which the program code may be stored as well as data information obtained during operation of the recording mechanism 60. The recording mechanism 60 may be provided with user communication elements 74 such as vibrating elements, audio generating elements capable of creating sounds and even voice messages.

The electronic circuit 64 is preferably arranged with a communication module 76 that is capable of transmitting and receiving data. Preferably the communication module 76 comprises modules for wireless communication with external mobile devices. Preferably, but not exclusively, the modules for wireless communication use short-range wireless technologies such as for example ANT+, Bluetooth, NFC, RFID, Wi-Fi, Wireless HART, ZigBee, Z-wave, etc. At present, Bluetooth technology is preferred, being widely spread and included in many so called smart mobile devices, but other communication technologies are naturally feasible.

The mobile devices may then either be capable of processing the data, such as e.g. calculating the time and date of an occurrence of the medicament delivery device, or may in turn transmit the monitored data to external databases via the communication technologies of the mobile device, such as cellular radio communication networks, e.g. GSM, 3G, 4G, etc. and/or wireless local area networks, which networks can provide access to the internet and thus to a large number of external data storage sources, data handling centres, etc. Regarding communication technologies, it is of course possible to incorporate the above mentioned communication technologies in the recording mechanism 60 as such.

A force sensor 80 is provided that in the embodiment is placed between a proximal surface of the end wall 12 of the outer housing 10 and a distally directed surface of the end wall 24 of the locking element 16. The force sensor 80 is operably connected to the electronic circuit 64 of the recording mechanism 60.

When the embodiment is to be used, the medicament delivery device 50 is entered into the proximal passage 18 of the locking element 16 while the release element 30 is pushed in the distal direction in order to allow ledges of the medicament delivery device to pass the ledges 22 of the arms 20 of the locking element 16. The distal end of the medicament delivery device will reach the support element 40 and compress the compression spring 48, which causes a force between the distal end of the locking element 16 and the distal end wall 12 of the outer housing 10, which is detected by the intermediate force sensor 80, which may wake up the electronic circuit 64 of the recording mechanism 60.

The medicament delivery device with its recording mechanism 60 is now ready to be used. The medicament delivery device may be arranged with a safety cap 52 at its proximal end, which has to be removed in order to use the medicament delivery device. The user then grips the safety cap 52 and pulls it in the proximal direction. The safety cap 52 may be attached with a friction fit to the proximal end of the medicament delivery device 50, which requires some force to pull the safety cap off the medicament delivery device. This in turn causes the force on the force sensor 80 to be reduced somewhat, which is detected and recorded by the recording mechanism 60. The detected signal may be used to indicate start of the dose delivery procedure, and/or it may be used to wake up the recording mechanism 60. A time stamp may be generated by the electronic circuit 64. The next step is to press the proximal end of the medicament delivery device 50 against a dose delivery site for e.g. a penetration by an injection needle. A force is thus exerted on the medicament delivery device in the distal direction which is transferred by the compression spring 48 to the force sensor 80 and detected and registered by the electronic circuit 64, creating a time stamp. This registration may be an indication that the dose delivery has started. Further, it is possible to measure or calculate the time between removal of the safety cap 52 and the penetration in order to obtain information regarding user behaviour such as how long has the user hesitated between removing the safety cap 52 and performing a penetration.

After the penetration, the medicament delivery device may automatically initiate an injection sequence, whereby a plunger rod 54 of a power pack 55 of the medicament delivery device 50 is released and is forced in the proximal direction by a drive spring 56. The plunger rod 54 will act on a stopper 57 inside a medicament container 58, whereby a dose of medicament is delivered to the dose delivery site through a medicament delivery member 59 such as an injection needle. The force during the injection may be detected by the force sensor 80 and possible changes in the force from the power pack 55 may provide indications on how well or smooth the stopper 57 is moving inside the medicament container 58, providing information regarding e.g. siliconisation of the medicament container 58. Further, the force detected when the medicament delivery device 50 is pressed against the dose delivery site may be used for initiating a user indication function that will inform and indicate to a user that the injection sequence is ongoing. In that regard, an audible signal or a tactile signal from the user communication elements 74 may be utilized during the injection sequence. Since the force sensor 80 may be capable of detecting the end of the injection sequence, this information may be used to either switch off the user communication elements 74 or calculate a certain time period after end of injection in which the medicament delivery device has to remain on the dose delivery site in order to ascertain complete delivery of the whole dose before the medicament delivery device can be removed. The user information may then continue during this additional time period in order to ascertain that the user does not remove the medicament delivery device prematurely. After the additional time period, the user communication elements 74 may be switched off, or additional user information may be provided instructing the user to remove the medicament delivery device from the dose delivery site.

The removal of the medicament delivery device will again be detected by the force sensor 80 because the force is reduced and is registered by the recording unit 70 in that the device is removed. The information may be used for measuring early removal, dwell time, holding the device too long etc.

All the information registered and stored by the recording unit may be transferred to external data handling functions. For instance, the information may be transferred to a smart device by the communication module 76 and the smart device may be provided with applications for handling the data and present it in a display of the smart device.

Figure 7:
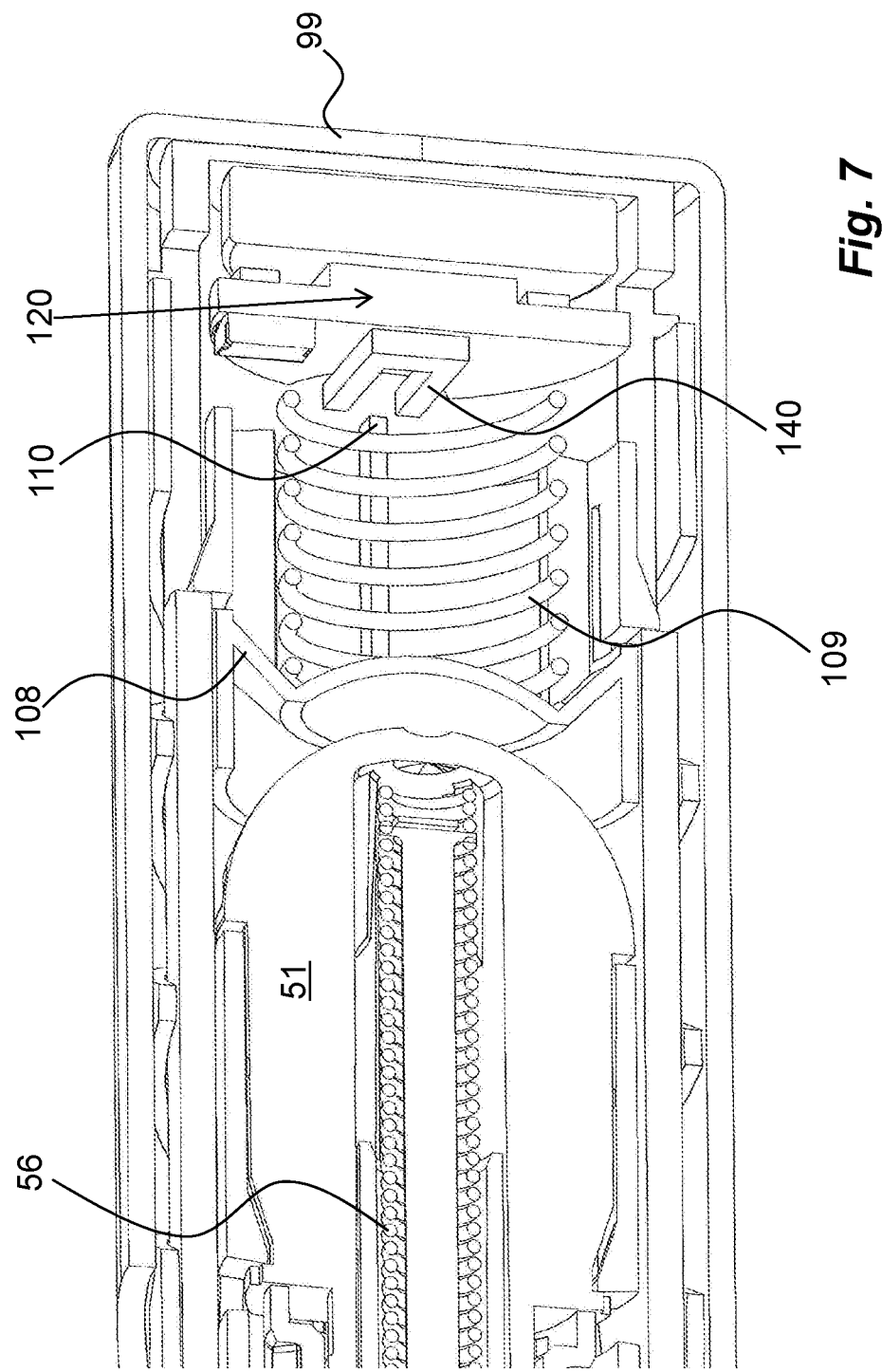

FIGS. 5-9 show another embodiment of a recording unit. One difference in comparison with the previous embodiment is that the outer housing 90 covers less of the medicament delivery device than the previous. A proximal end of the outer housing 90 is arranged with a passage 92 through which a front part of the medicament delivery device 50 can protrude. As with the previous embodiment, it comprises a locking element 94 that can releasably hold the medicament delivery device via flexible arms 96 having ledges 98 that grip around ledges on the medicament delivery device, which locking element further comprises a distal end wall 99, FIGS. 5 and 7. Further, a release element 100 is provided that can provide a release of the flexible arms 96 when a protrusion 102 extending through an elongated opening 104 in the housing is manually operated by a user. The release element 100 is further arranged with the same type of resilient area 106 as for the previous embodiment. Moreover, a support element 108 is arranged slidable inside the locking element 94. The support element 108 is urged in the proximal direction to an initial position by a support element spring that in the embodiment shown is a compression spring 109. The locking element 94 is also urged in the proximal direction by wedge-shaped protrusions 111 of the support element 108 acting on the edges of the rectangular cut-outs 28. The support element 108 is in this embodiment arranged with two distally directed pins 110, FIG. 6 that are to interact with sensors 140 of a recording mechanism 120 as will be described below. In the initial position of the support element 108 as seen in FIG. 7, the pins 110 are out of engagement with the sensors 140.

The recording mechanism 120 is arranged at a distal end of the locking element 94. As with the previous recording mechanism, the recording mechanism 120 comprises a printed circuit board 122 provided with an electronic circuit 124. On the distal side of the printed circuit board 122, support elements 126 are arranged providing a space between the distal surface of the printed circuit board 122 and a power source 128 in the form of a button cell. The distal surface of the button cell 128 is in contact with a proximally directed surface of the end wall 99 of the locking element 94. The electronic circuit 124 is provided with a micro-controller unit 130 or MCU arranged to perform different functions based on program code. The electronic circuit 124 is further arranged with memory storage elements 132 in which the program code may be stored as well as data information obtained during operation of the recording mechanism 120. The recording mechanism 120 may be provided with user communication elements 134 such as vibrating elements, audio generating elements capable of creating sounds and even voice messages.

The electronic circuit 124 is preferably arranged with a communication module 136 that is capable of transmitting and receiving data. Preferably the communication module 136 comprises modules for wireless communication with external devices. Preferably, but not exclusively, the modules for wireless communication use short-range wireless technologies such as for example ANT+, Bluetooth, NFC, RFID, Wi-Fi, Wireless HART, ZigBee, Z-wave, etc. At present, Bluetooth technology is preferred, being widely spread and included in many so called smart devices, but other communication technologies are naturally feasible. The recording mechanism 120 is further arranged with motion sensors 140 that in the embodiment shown are photo-electric sensors having a fork-shape. They are positioned such as to be able to detect the pins 110 of the support element 108 as will be explained.

When the monitoring unit is to be used with a medicament delivery device, a distal end of the medicament delivery device 50 is entered into the proximally directed passage of the locking element 94. The release element 100 has before that being pushed manually in the distal direction against the resilient force of the resilient area 106 of the release element. This enables the proximally directed arms 96 of the locking element 94 to flex radially outwards, enabling the passing of a ledge 98 around a window on the medicament delivery device 50. During the pushing of the medicament delivery device 50 in the distal direction, an end cap 51 on its distal end will come in contact with the support element 108 and move it in the distal direction against the force of the support element spring 109, wherein the end cap 51 is pushed tightly in contact with a distal end of the housing of the medicament delivery device 50. When now the medicament delivery device is in position, the ledges 98 of the arms 96 lock the medicament delivery device. Further, the movement of the support element 108 in the distal direction has caused the pins 110 to move into the forks of the photo electric sensors 140, whereby the recording mechanism 120 is activated.

Figure 8:
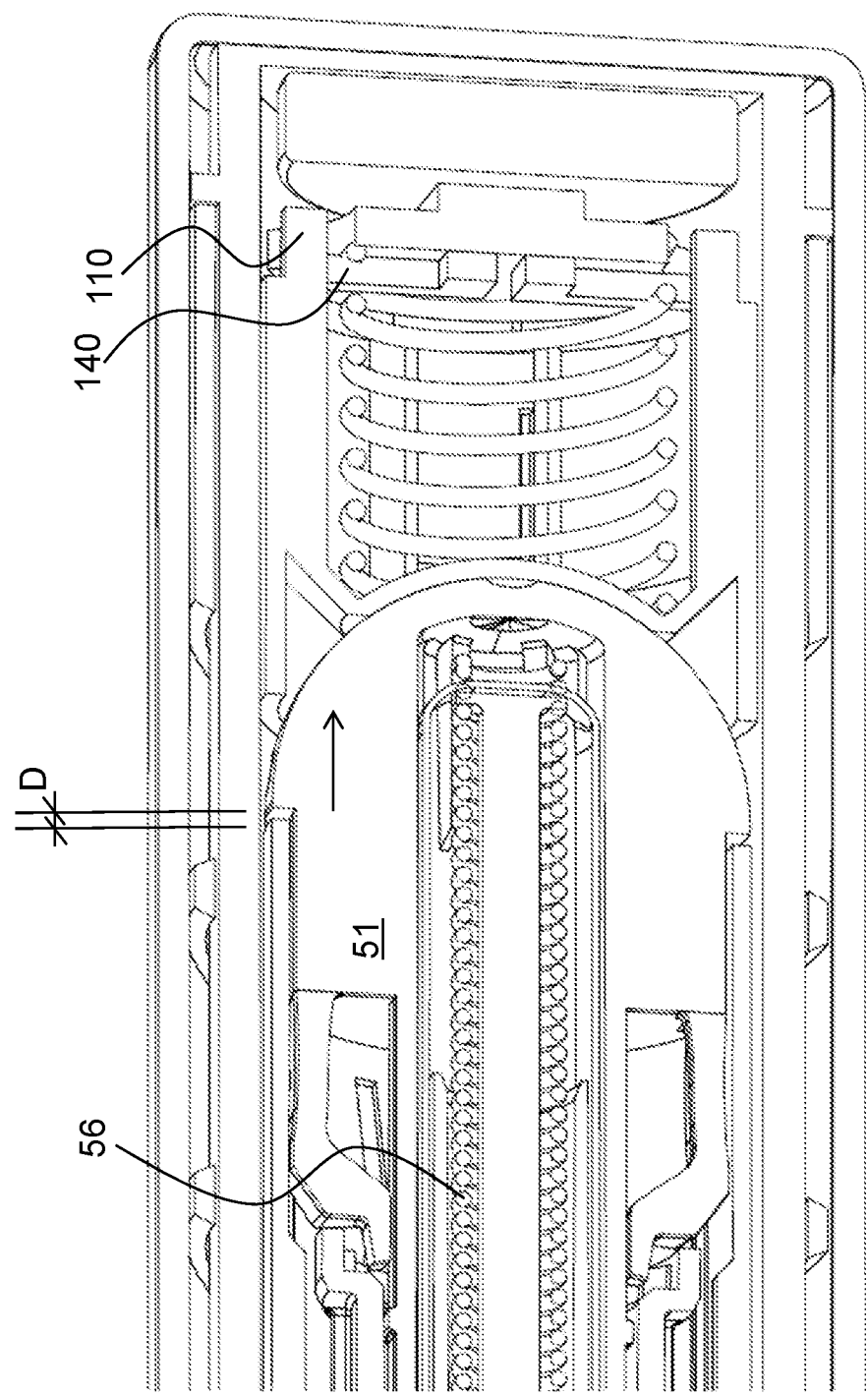
Figure 9:
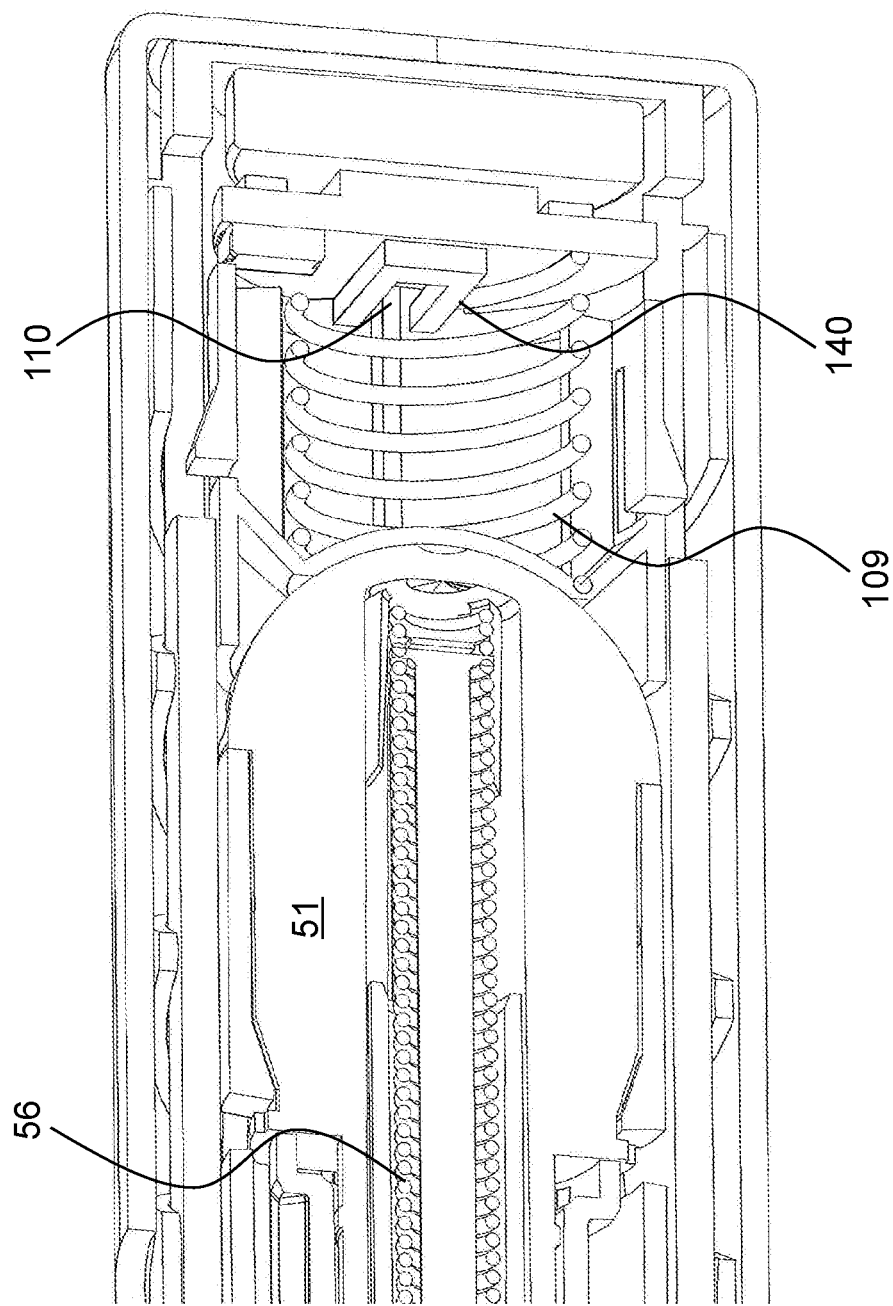

In order to deliver a dose of medicament, the medicament delivery device is pressed against a dose delivery site. As mentioned above this will cause the power pack 55 of the medicament delivery device to be released such that the drive spring 56 forces the plunger rod 54 in the proximal direction, wherein the plunger rod 54 acts on the stopper 57 inside the medicament container 58, which in turn causes expelling of a dose of medicament through the medicament delivery member 59 at the dose delivery site. As seen in FIG. 7, the distal end of the drive spring 56 is in contact with the distal end cap 51 of the medicament delivery device 50. The end cap 51 is movable distally in relation to the housing a small distance D and will do so when the drive spring of the power unit is released as seen in FIG. 8. This small movement is transferred to the support element 108 due to the connection and against the force of the support element spring 109, and this small movement is detected by the photo electric sensors 140. The detection by the photo sensors is registered by the electronic circuit. Thus, the start of the injection is recorded by the recording mechanism 120, providing for example a time stamp and starting a timer.

The drive spring 56 pushes the plunger rod 52 and the stopper 57 until the stopper 57 reaches the proximal end inside the medicament container 58. At this position, the force of the drive spring 56 is reduced compared to the start force, and the force of the support element spring 109 is chosen such in relation to the drive spring 56 that the force of the support element spring 109 is larger than the force of the drive spring 56, whereby the end cap 51 is pushed back to its initial position via the support element 108. The movement of the support element 108 is again detected by the photo electric sensors 140 and registered by the recording mechanism 120 as the end of injection sequence. Again the recording mechanism 120 may provide a time stamp and register time elapsed since the previous time stamp.

The recording unit may then use the time stamps and the timer information for producing different kind of information regarding user behaviour. One may be to register what day the dose delivery has taken place and may also calculate when a subsequent dose should be administered based on predefined schedules. The recording unit may further provide information directly to a user via a user communication element, for example when the injection has ended, by providing audible, tactile or visual input. The information registered and calculated by the recording unit may be transferred to external data handling functions. One such function could be a smart device that a user has, with possibly an application that can handle the information obtained from the recording unit.

It is to be understood that the invention described above and disclosed in the drawings is to be regarded only as a non-limiting example and that it is defined by the scope of the patent claims.

The invention claimed is:

1. A recording unit arranged to be connected to a medicament delivery device, which recording unit comprises:
   a generally elongated housing having dimensions so as to enclose at least a distal part of the medicament delivery device,
   a support element positioned inside the housing and located at a distal end of the housing, where the support element comprises a transversal wall,
   the recording unit comprising a recording mechanism provided with an electronic circuit and arranged at a distal end inside the housing,
   a compression spring having a proximal end abutting the transversal wall and having a distal end abutting the recording mechanism such that the spring exerts a force on the support element biasing the support element in a proximal direction,
   the electronic circuit comprising an activation element operably arranged to activate the electronic circuit when the medicament delivery device is inserted in the housing,
   the electronic circuit comprising a sensor element capable of sensing status changes of said medicament delivery device during use.

2. The recording unit according to claim 1, further comprising
   a locking element for locking the medicament delivery device in the proximal direction when inserted into the housing.

3. The recording unit according to claim 2, wherein the locking element comprises a proximal passage provided with a first and a second proximally extending arms.

4. The recording unit according to claim 3, wherein both the first and the second proximally extending arms comprise at least one radially inwardly protruding ledge.

5. The recording unit according to claim 2, further comprising a holding element for releasably holding the locking element in a locking position.

6. The recording unit according to claim 5, wherein the holding element comprises an area with removed material forming a band shaped structure that provides a resiliency between a proximal part and a distal part of the holding element.

7. The recording unit according to claim 6, wherein the holding element comprises an outwardly extending protrusion arranged to fit into an elongated passage on a surface of the generally elongated housing.

8. The recording unit according to claim 5, wherein the holding element is arranged to fit into and coaxial with the generally elongated housing.

9. The recording unit according to claim 1, wherein the holding element is arranged slidable inside the housing between
   a holding position where the locking element is in a locking position, and
   a release position wherein the locking element may be moved out of engagement with the medicament delivery device.

10. The recording unit according to claim 1 wherein the sensor element comprises a force sensor capable of sensing force variations in the medicament delivery device during use.

11. The recording unit according to claim 1, wherein the sensor element comprises a movement sensor capable of sensing movement of the medicament delivery device relative the recording unit during use.

12. The recording unit according to claim 11, wherein the movement sensor is capable of sensing movement of components of the medicament delivery device.

13. The recording unit according to claim 1, further comprising at least one user communication element capable of providing a user with information regarding the status of the medicament delivery device.

14. The recording unit according to claim 13, wherein the user communication element is capable of providing audible tactile information.

15. The recording unit according to claim 13, wherein the user communication element is capable of providing tactile information.

16. The recording unit according to claim 1, further comprising a communication module capable of communicating with at least one external communication device.

17. The recording unit according to claim 16, wherein the communication module comprises near range communication technology.

18. The recording unit according to claim 16, wherein the communication module comprises cellular radio communication technology.

19. The recording unit according to claim 16, wherein the communication module comprises wireless local area network communication technology.

20. The recording unit according to claim 1, wherein the medicament delivery device has an outer distal end having a defined shape and the transversal wall further comprises a proximal facing portion that is configured to correspond to the defined shape of the outer distal end of the medicament delivery device.

* * * * *